United States Patent
Ray et al.

(10) Patent No.: US 6,586,598 B2
(45) Date of Patent: Jul. 1, 2003

(54) α,α-DIBROMO-α-CHLORO-ACETOPHENONES AS SYNTHONS

(75) Inventors: Anup K. Ray, Staten Island, NY (US); Hiren Patel, Edison, NJ (US); Shilpa V. Merai, North Brunswick, NJ (US); Mahendra R. Patel, East Brunswick, NJ (US)

(73) Assignee: Geneva Pharmaceuticals, Inc., Broomfield, CO (US)

( * ) Notice: Subject to any disclaimer, the term of this patent is extended or adjusted under 35 U.S.C. 154(b) by 0 days.

(21) Appl. No.: 10/140,638

(22) Filed: May 8, 2002

(65) Prior Publication Data

US 2002/0188130 A1 Dec. 12, 2002

Related U.S. Application Data

(62) Division of application No. 09/614,295, filed on Jul. 12, 2000, now Pat. No. 6,458,957.

(51) Int. Cl.[7] ............... C07D 211/32; C07D 211/40; C07D 211/82; C07D 49/214; C07D 49/237
(52) U.S. Cl. ............... 546/220; 546/233; 546/337; 568/308; 568/309; 568/335
(58) Field of Search ............... 568/308, 309, 568/335; 546/220, 233, 337

(56) References Cited

U.S. PATENT DOCUMENTS

| | | |
|---|---|---|
| 4,005,209 A | 1/1977 | Banitt et al. |
| 4,617,396 A | 10/1986 | Leir |
| 4,642,384 A | 2/1987 | Leir |
| 4,650,873 A | 3/1987 | Leir |
| 4,684,733 A | 8/1987 | Leir |

FOREIGN PATENT DOCUMENTS

| | | |
|---|---|---|
| DD | 200709 | 6/1983 |
| PL | 85387 | 4/1973 |
| PL | 89232 | 4/1973 |

OTHER PUBLICATIONS

Suzuki, et al. Synthesis (1984) pp. 499–500.
Idoux et al. J. Org. Chem., vol. 48, No. 21 (1983) pp. 3771–3773.
McKillop, et al. Synthetic Communications, 4(1), (1974) pp. 35–43.
Gupton, et al. Synthetic Communications, 12(9), (1982) pp. 695–699.
Kornblum, et al. J. Org. Chem., vol. 41, No. 9 (1976) pp. 1560–1564.
Shaw, et al. J. Org. Chem., vol. 41, No. 4, (1976) 2 pgs.
Bacon, et al. J. Chem. Soc. (C), (1969) pp. 312–315.
Bohdan Sledzinski, et al., Rocz. Chem. (1976), 50(5) pp. 979–986 plus Chemical Abstract 1977:43333.
Chemical Abstract 1979:121213 of PL 85387.
Chemical Abstract 1978:423935 of PL 89232.
Chemical Abstract 1983:535552 of DD 200709.

*Primary Examiner*—Alan L. Rotman
*Assistant Examiner*—Raymond Covington
(74) *Attorney, Agent, or Firm*—Gabriel Lopez

(57) ABSTRACT

This disclosure relates to the use of α,α-dibromo-α-chloroacetophenone compounds as intermediates for the preparation of aromatic carbonyl compounds, especially aromatic amides. The compound 2,5-bis(2,2,2-trifluoroethoxy)-α,α-dibromo-α-chloroacetophenone is especially useful as an intermediate for the preparation of flecainide, a known pharmaceutical.

15 Claims, No Drawings

α, α-DIBROMO-α-CHLORO-ACETOPHENONES AS SYNTHONS

This is a division of Ser. No. 09/614,295, Jul. 12, 2000, now U.S. Pat. No. 6,458,957.

SUMMARY

α,α-Dibromo-α-chloro acetophenone compounds are reacted with nucleophiles to yield aromatic carbonyl compounds. In an important aspect, 2,5-bis(2,2,2-trifluoroethoxy)-N-(2-piperidylmethyl)-benzamide is prepared by reacting 2,5-bis(2,2,2-trifluoroethoxy)-α,α-dibromo-α-chloro acetophenone with 2-(2-aminomethyl) pyridine and reducing the piperidine ring.

BACKGROUND 2,5-bis(2,2,2-trifluoroethoxy)-N-(2-piperidylmethyl)-benzamide (III) is a known medicament useful for the treatment of arrhythmia and is described in U.S. Pat. No. 3,900,481. It is commercially available as its acetate salt. Methods for its synthesis are described, for example, in U.S. Pat. Nos. 4,642,384 and 4,617,396.

The synthetic method described in U.S. Pat. No. 4,642,384 involves the preparation of 2,5-bis(2,2,2-trifluoroethoxy)-.,a-dichloroacetophenone as an intermediate by chlorinating the a-unsubstituted 2,5-bis(2,2,2-trifluoroethoxy)acetophenone with chlorine gas at a moderate temperature, such as 50-60° C. The α,α-dichloroacetophenone intermediate is further chlorinated in the presence of a buffering base, such as sodium acetate, at a slightly higher temperature, such as 80-100° C. to yield the α,α,α-trichloroacetophenone. The α,α,α-trichloroacetophenone is reacted with 2-aminomethylpyridine to yield a benzamide, and the pyridine ring is reduced to yield 2,5-bis(2,2,2-trifluoroethoxy)-N-(2-piperidylmethyl)-benzamide.

The inventive process is based on the discovery that the α,α-dibromo-α-chloroacetophenone is easily prepared in high yield and purity under mild conditions, and that it is a superior leaving group in nucleophilic substitution reactions.

DETAILED DESCRIPTION

In one aspect this invention relates to a process for preparing the anti-arrhythmic agent, 2,5-bis(2,2,2-trifluoroethoxy)-N-(2-piperidylmethyl)-benzamide (III), commonly known as flecainide, and pharmaceutically acceptable salts thereof, in particular the acetate salt.

The synthetic route comprises the reaction of 2,5-bis(2,2,2-trifluoroethoxy)-α,α-dibromo-α-chloro acetophenone (I) with 2-(aminomethyl)pyridine to form the corresponding benzamide (II). The pyridyl ring of the benzamide (II) is then reduced to the piperidinyl moiety yielding the desired compound, flecainide acetate (III). The reaction scheme with preferred reagents is set forth below:

Step 1:

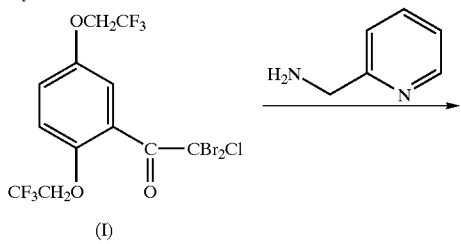

(I)

Since the bulky dibromochloromethyl group is an excellent leaving group, (I) undergoes a facile amidization reaction with 2-aminomethylpyridine under mild conditions, such as at room temperature. It is preferred to carry out the reaction in an inert, non-polar solvent, such as toluene, hexane and the like, preferably a mixture of toluene and hexane.

Step 2:

(II)

(III)

The reduction of pyridine rings to piperidine rings is well known and can be effected many means, such as hydrogenation, or reduction with a metal hydride, a metal or dithionite. Hydrogenation is carried out by contacting a solution of the benzamide (II) with hydrogen in the presence of a hydrogenation catalyst, such as Pt/C, Pt, Pt/PtO$_2$ Pd/C, Rh/C, or Raney nickel. However, since it is unnecessary to protect any of the other functional groups in the molecule when the reduction is carried out by hydrogenation with a platinum-carbon catalyst, and since yields and purity are excellent, hydrogenation with a platinum-carbon catalyst is preferred.

Alternatively, for the preparation of flecainide, 2,5-bis(2,2,2-trifluoroethoxy)-Q,(α, α-dibromo-α-chloro acetophenone (I) can be reacted directly with 2-aminomethylpiperidine, avoiding the reduction step. However, the formation of impurities makes the two step synthetic scheme described above preferable.

This invention further relates to the synthon 2,5-bis(2,2,2-trifluoroethoxy)-α,α-dibromo-α-chloro acetophenone (I). The bulky dibromochloromethyl group is an excellent leaving group for nucleophilic substitution reactions.

2,5-bis(2,2,2-trifluoroethoxy)-α,α-dibromo-α-chloro acetophenone (1) is preferably prepared from 2,5-bis(2,2,2-trifluoroethoxy)-α-chloro-acetophenone by reaction with bromine, preferably under neutral or acidic conditions, such as in glacial acetic acid in the presence of sodium acetate. Alternatively, other bromination methods, such as reaction with an N-bromoamide like N-bromosuccinimide, are also useful.

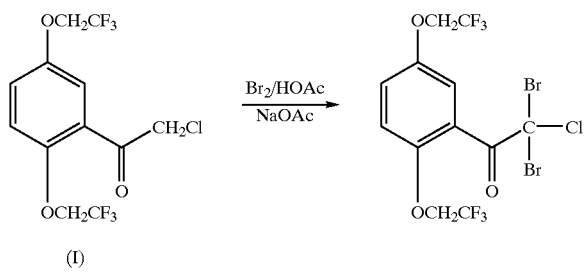

(I)

The 2,5-bis(2,2,2-trifluoroethoxy)-α-chloro-acetophenone starting material is prepared by known methods. For example, a monochloro acetyl group is introduced to the ortho position of 1,4-bis(2,2,2-trifluoroethoxy)-benzene by a Friedel Crafts reaction using 2-chloroacetylchloride and a Lewis acid catalyst, such as tin chloride, ferric chloride or preferably, aluminum chloride, in the presence of a chlorinated hydrocarbon solvent, preferably methylene chloride.

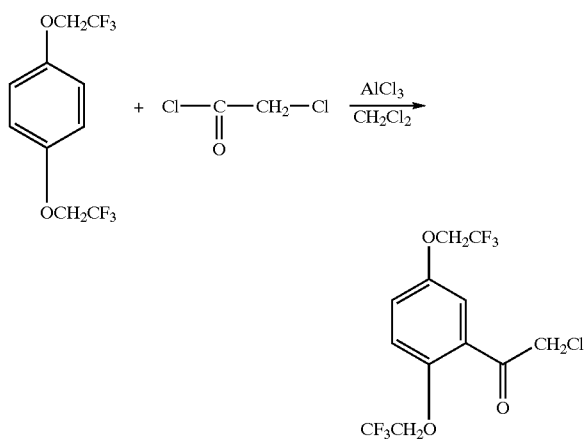

The 1,4-bis(2,2,2-trifluoroethoxy)-benzene in turn is prepared by reacting 1,4-dibromobenzene with sodium 2,2,2-trifluoroethoxylate in the presence of cupric bromide as described in U.S. Pat. Nos. 4,684,733 and 4,650,873, which are here incorporated by reference.

The present invention further relates to the use of an α,α-dibromo-α-chloro acetophenone as a reagent in nucleophilic substitution reactions whereby the bulky dibromo-chloromethyl group is a leaving group that is replaced by a nucleophile, such as an amine, an alcohol, a mercaptan, an amide or a carbanion-forming compound. Particularly interesting carbanion forming compounds are carbonyl compounds having an α-hydrogen atom, for example, ketones and esters having a methyl or methyene group adjacent to the carbonyl group, and Grignard reagents. Thus, the present invention includes a process for preparing an aromatic carbonyl compound, which comprises (a) preparing an α,α-dibromo-α-chloro derivative of an acetophenone compound and (b) reacting the α,α-dibromo-α-chloro derivative of the acetophenone compound with an amine, an alcohol, a mercaptan, an amide or a carbanion-forming compound.

The instance where the aromatic carbonyl compound is a benzamide is an important process of the present invention.

Thus, the present invention further relates to a process for preparing a benzamide which comprises reacting an α,α-dibromo-α-chloro acetophenone compound with a primary or secondary amine.

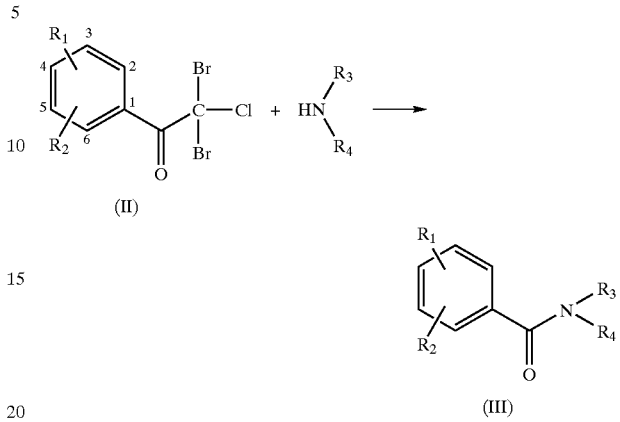

The phenyl ring of the α,α-dibromo-α-chloro acetophenone compound is unsubstituted or substituted by $R_1$ and $R_2$ substituents which are independently, for example, hydrogen, $C_1$-$C_6$-alkyl, $C_3$-$C_7$-cycloalkyl, $C_1$-$C_6$-alkoxy, —N($C_1$-$C_6$-alkyl)$_2$, —S—$C_1$-$C_6$-alkyl, or phenyl; wherein the alkyl groups are unsubstituted or substituted by one or more halogen, hydroxy, —S-alkyl, —O-alkyl, carboxy, amido, or ester groups and when $R_1$ or $R_2$ is a phenyl substituent it is unsubstituted or substituted in the phenyl ring by halogen, $C_1$-$C_6$-alkyl, $C_3$-$C_7$-cycloalkyl, $C_1$-$C_6$-alkoxy, —N($C_1$-$C_6$-alkyl)$_2$, or —S—$C_1$-$C_6$-alkyl wherein the alkyl groups are unsubstituted or substituted by one or more halogen, hydroxy, —S-alkyl, —O-alkyl, carboxy, amido, or ester groups; or $R_1$ and $R_2$ together with the phenyl ring carbons to which they are attached form a 5-7 member aliphatic, aromatic, heterocyclic or heteroaromatic ring.

One embodiment includes those compounds wherein the phenyl ring of the α,α-dibromo-α-chloro acetophenone compound is unsubstituted or substituted by $R_1$ and $R_2$ substituents which are independently hydrogen, $C_1$-$C_6$-alkyl, $C_3$-$C_7$-cycloalkyl, $C_1$-$C_6$-alkoxy, —N($C_1$-$C_6$-alkyl)$_2$, or —S—$C_1$-$C_6$-alkyl; wherein the alkyl groups are unsubstituted or substituted by one or more halogen, hydroxy, —S-alkyl, —O-alkyl, carboxy, amido, or ester groups. An alternate embodiment include those compounds wherein $R_1$ and $R_2$ are independently hydrogen, $C_1$-$C_4$-alkyl, $C_3$-$C_7$-cycloalkyl, or $C_1$-$C_4$-alkoxy wherein the alkyl groups are unsubstituted or substituted by one or more halogen, hydroxy, or —O-alkyl substituents. Further alternate embodiments include those compounds wherein at least one of $R_1$ and $R_2$ is substituted or unsubstituted $C_1$-$C_4$-alkyl; substituted or unsubstituted $C_3$-$C_7$-cycloalkyl; substituted or unsubstituted $C_1$-$C_4$-alkoxy; substituted or unsubstituted —N($C_1$-$C_4$-alkyl)$_2$; or substituted or unsubstituted —S—$C_1$-$C_4$-alkyl.

Preferably, $R_1$ is in the 4-position when $R_2$ is hydrogen, or $R_1$ is in the 2-position and $R_2$ is in the 5-position when $R_2$ is other than hydrogen.

The nitrogen substituents, $R_3$ and $R_4$, are independently, for example, hydrogen or unsubstituted $C_1$-$C_6$-alkyl or $C_1$-$C_6$-alkyl which is substituted by one or more of, for example, —OH, halogen, alkoxy, or an aliphatic, aromatic, heterocyclic or heteroaromatic ring; or $R_3$ and $R_4$ together with the nitrogen atom form a heterocyclic ring such as a piperidine, piperazine, pyrrole, or morpholine ring.

Examples of suitable α,α-dibromo-α-chloro acetophenone compounds include 2-hydroxy-5-chloro-α,α-dibromo-α-chloro acetophenone which is reacted with 2-chloro-4-nitro-aniline to yield the therapeutic agent niclosamide.

The present invention further relates to α,α-dibromo-α-chlorophenone compounds of the formula

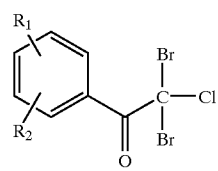

(II)

wherein $R_1$ and $R_2$, and the embodiments thereof, are described above. The compounds are useful as intermediates for the preparation of aromatic carbonyl compounds.

The following examples are intended to illustrate, but not limit, the inventive process.

EXAMPLE 1

1,4-Bis(2,2,2-Trifluoroethoxy)-Benzene 30.0 g (0.75 mole, 60% dispersion in oil) of anhydrous sodium hydride is added to a three-necked round bottom flask (500 mL) fitted with a condenser a with $CaCl_2$ guard tube, a nitrogen inlet and a dropping funnel. 160 ml of dry dimethylformamide is added to make a slurry. The slurry is cooled in ice water and 2,2,2-trifluoroethanol (75 mL, 1.03 mole) is added dropwise resulting in an exothermic reaction. The temperature inside the flask is maintained below 30° C. During the addition of 2,2,2-trifluoroethanol, the mixture first becomes yellow in color and then becomes a brown clear solution. After the addition of the 2,2,2-trifluoroethanol is complete, the reaction mixture is stirred at room temperature for 30 minutes under a nitrogen blanket. 30.0 g (0.13 mole) of 1,4-dibromobenzene and 3.75 g of cupric bromide are then added. The resulting mixture is heated to 100° C. with vigorous stirring for 2.5 hours. The reaction mixture is then cooled to room temperature and quenched with ice-water (1500 mL). The aqueous phase is acidified with about 50-55 ml of concentrated HCl. The resulting solid is filtered with vacuum and washed with copious amount of water. The violet-colored solid is dried overnight under vacuum in a desiccator over $P_2O_5$. The dried solid is dissolved in diethylether and filtered. The filtrate is evaporated resulting in a off-white solid (34.5 g, yield 99%) which is crystallized in n-hexane to yield needle-shaped crystals of 1,4-bis(2,2,2-trifluoroethoxy)-benzene.

m.p. 74-77° C.

MS: $M^+274$ (EI-MS)

$^1$H NMR ($CDCl_3$): δ 4.32 (4H,q,2,5-O—$CH_2$—$CF_3$), δ 6.91 (4H,s, 1,3,4,6-H)

EXAMPLE 2

2,5-Bis(2,2,2-Trifluoroethoxy)-α-Chloro Acetophenone

A two necked round bottom flask (250 mL) is fitted with a nitrogen inlet and a dropping funnel and 6.0 g (0.045 mole) of anhydrous aluminum chloride and 50.0 mL of dry methylchloride are added. A solution of 10.0 g (0.0365 mole) of 1,4-bis(2,2,2-trifluoroethoxy)benzene dissolved in dichloromethane (10 mL) is added dropwise at room temperature with stirring followed by 4.0 mL (0.05 mole) of 2-chloroacetylchloride. The color of the solution slowly changes to red-brown. The mixture is stirred at room temperature for 2.5 hours. The red-brown colored solution is poured into a mixture of ice water (200 mL) and 15.0 mL concentrated HCl and stirred for 20 minutes. The pink dichloromethane phase is separated, and the aqueous phase is extracted with dichloromethane (50 mL×2). The combined dichloromethane phases are washed with: i) $H_2O$ (100 mL×2) ii) 5% NaOH (50 mL×2) and iii) $H_2O$ (100 mL×2) and the resulting yellow solution is dried over anhydrous sodium sulfate and then evaporated under reduced pressure resulting in a yellow solid (11.5 g, yield 90%). Crystallization from n-hexane results in a shining white crystals of 2,5-bis(2,2,2-trifluoroethoxy)-a-chloroacetophenone.

m.p. 76-78° C.

MS: $M^+350$ (EI-MS)

$^1$H NMR: δ 4.38 (2H,q,5-O—$CH_2$—$CF_3$), δ 4.48 (2H,q,-2-O—$CH_2$—$CF_3$), δ 4.75 (2H,s, 1'—C=O—$CH_2$—Cl), δ 6.9 (1H,o-d, J=9.1 Hz, 3-H), δ 7.2 (1H,o-m-dd, Jo-m=8.6, 3.1 Hz, 4-H), δ 7.48 (1H, m-d, Jm=3.1 Hz, 6-H)

EXAMPLE 3

2,5-Bis(2,2,2-Trifluoroethoxy)-α,α-Dibromo-α-Chloro Acetophenone 2.0 g (0.0057 mole) of 2,5-bis(2,2,2-trifluoroethoxy)-a-chloroacetophenone, 2.8 g (0.034 mole) of anhydrous sodium acetate and 12.0 mL of glacial acetic acid are added to a 100 ml two necked round bottom flask. The mixture is stirred and heated to 70° C. in an oil bath. 0.63 mL (0.0113 mole) of bromine are added dropwise maintaining the temperature at about 65-70° C., and the mixture is allowed to react for about one hour. The mixture is monitored by TLC (solvent system=ethyl acetate:hexane 4:1) until no 2,5-bis (2,2,2-trifluoroethoxy)-α-chloroacetophenone remains. When the reaction is completed, the solution is poured into 100 mL of ice water, and the aqueous fraction is extracted with dichloromethane (15 mL×3). The organic phase is then washed with: i) 5% $NaHCO_3$ (10 mL×2) and ii) deionized $H_2O$ (15 mL×2) and then dried over anhydrous $Na_2SO_4$. Evaporation of the dichloromethane under reduced pressure results in a thick syrupy liquid which solidifies when cooled. Washing with n-hexane yields 2,5-bis(2,2,2-trifluoroethoxy)-α,α-dibromo-α-chloro acetophenone as a brown solid (2.8 g, yield 98%).

m.p. 42-43° C.

MS: $M^+506$ (EI-MS), $(M+H)^+507$ (Cl-MS)

$^1$H NMR ($CDCl_3$): δ 4.5 (4H, two quartet merge, 2,5-O—$CH_2$—$CF_3$), δ 6.97 (1H,o-d, J=9.2 Hz, 3-H),δ 7.09 (1H,o, m-dd, J=9.2, 3.1 Hz, 4-H), δ 7.35 (1H, m-d, J=3.1 Hz, 6-H)

EXAMPLE 4

2,5-Bis(2,2,2-Tri Fluoroethoxy)-N-(2-Pyridylmethyl)-Benzamide 12.0 g (23.7 mmoles) of 2,5-bis(2,2,2-trifluoroethoxy)-α,α-dibromo-α-chloro acetophenone is added to a 250 ml round bottom flask and dissolved in 14.5 mL of toluene and stirred at room temperature. 2.82 g (26.07 mmoles) of 2-(aminomethyl)-pyridine are shaken with a solvent mixture, hexane:toluene (5:1, 50.0 mL), and added to the round bottom flask over a period of about 20 minutes. When the addition is about half complete, a precipitate appears and makes stirring difficult. After the addition is completed, another 50.0 mL of hexane:toluene (5:1) mixture is added, and the mixture is stirred vigorously for another 3 hours. The reaction mixture is filtered yielding a light yellow solid which is washed with n-hexane yielding 2,5-bis(2,2,2-trifluoroethoxy)-N-(2-pyridylmethyl)-benzamide as an off-white solid (9.02 g, yield 93.4%).

m.p. 100-103° C.

MS: M$^+$408 (El-MS), (M+H)$^+$409 (CI-MS)

$^1$H NMR (CDCl$_3$): δ 4.4 (2H,q, 2-O—CH$_2$—CF$_3$), δ 4.5 (2H,q, 5-O—CH$_2$—CF$_3$), δ 4.8 (2H,d, 7'-H), δ 6.95 (1H,o-d, J=9.1 Hz, 3-H), δ 7.1 (1H,dd, J=3.0, 8.9 Hz, 4-H), δ 7.22 (1H,dd, J=5.4, 7.2 Hz, 4'-H), δ 7.32 (1H, d, J=7.9 Hz, 5'-H), δ 7.7 (1H, dd, J=1.8, 7.7 Hz, 3'-H), δ 7.8 (1H, d, J=3.4 Hz, 6-H), δ 8.56 (1H, d, J=4.4 Hz, 2'-H), δ 8.6 (1H, br.s., 8'-H)

EXAMPLE 5

2,5-Bis(2,2,2-Trifluoroethoxy)-N-(2-Piperidylmethyl)-Benzamide Acetate 5.0 g (0.01225 mole) of 2,5-bis(2,2,2-trifluoroethoxy)-N-(2-pyridylmethyl)-benzamide is dissolved in 30 mL glacial acetic acid in a pressure vessel (Parr Instrument Company). 0.515 g Pt-C (5% wt./wt.) is added to the vessel. The vessel is flushed with nitrogen and then with hydrogen. The solution is stirred for 23 hours with under hydrogen at a pressure of 30 lbs. The solution is then filtered on celite and washed with isopropyl alcohol. The filtrate is evaporated under reduced pressure. The resulting syrupy liquid is shaken vigorously with n-hexane to yield a yellowish white precipitate which is washed with ether yielding an off-white solid. The solid 2,5-bis(2,2,2-trifluoroethoxy)-N-(2-piperidylmethyl)-benzamide acetate is dried in the vacuum dessicator over P$_2$O$_5$ (4.5 g, 89% yield) and then crystallized from isopropyl alcohol and isopropyl ether.

m.p. 149-151° C.

MS: CI-MS), (M+H)$^+$415

$^1$H NMR (CD$_3$OD): δ 1.45-2.1 (6H,m, 3',4',5'-H), δ 2.9 (1H,m, 6'-H), δ 3.2-3.45 (2H, br.d, m, 2'-H), δ 3.6 (2H,m, 7'-H), δ 4.54 (2H,q, 2-O—CH$_2$—CF$_3$), δ 4.7 (2H,q, 5-O—CH$_2$—CF$_3$), δ 7.2 (2H, s, 3-H, 4-H), δ 7.48 (1H, s, 6-H)

EXAMPLES 6-14

The α,α-dibromo-α-chloroacetophenone compounds set forth below are prepared in accordance the procedure set forth in Example 3 starting with the appropriately substituted α-chloroacetophenone:

TABLE 1

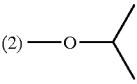

(II)

| # | R$_1$ | R$_2$ |
|---|---|---|
| 6 | (2) —OCH$_3$ | (5) —OCH$_3$ |
| 7 | (2) —O—CH(CH$_3$)$_2$ | (5) —O—CH(CH$_3$)$_2$ |
| 8 | (2) —O—CH$_2$—C(CH$_3$)$_3$ | (5) —O—CH$_2$—C(CH$_3$)$_3$ |
| 9 | (2) —OCH$_3$ | (5) —OCH$_2$CH$_3$ |
| 10 | (4) —Cl | H |
| 11 | (4) —Br | H |
| 12 | (4) —CH$_3$ | H |
| 13 | H | H |
| 14 | (4) —OCH$_3$ | H |

EXAMPLE 15-20

The compounds in Table 2 are prepared by reacting the α,α-dibromo-α-chloroacetophenone compounds prepared above with the nucleophiles identified in Table 2 by a procedure analogous to that described in Example 4:

TABLE 2

| # | acetophenone | nucleophile | product |
|---|---|---|---|
| 15 | Example 3 | HN(CH$_3$)$_2$ | 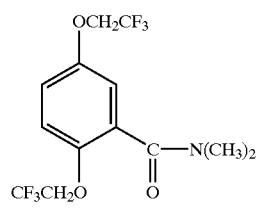 |
| 16 | Example 6 | piperidine | 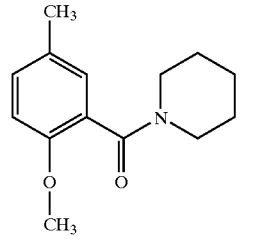 |

TABLE 2-continued

| # | acetophenone | nucleophile | product |
|---|---|---|---|
| 17 | Example 6 | N-methylpiperazine | 2-methoxy-5-methylphenyl (4-methylpiperazin-1-yl) methanone |
| 18 | Example 6 | 2-aminomethyl-N-methylpiperidine | 2-methoxy-5-methyl-N-((1-methylpiperidin-2-yl)methyl)benzamide |
| 19 | Example 3 | morpholine | (2,5-bis(2,2,2-trifluoroethoxy)phenyl)(morpholino)methanone |
| 20 | Example 3 | 2-aminomethyl-N-methylpiperidine | 2,5-bis(2,2,2-trifluoroethoxy)-N-((1-methylpiperidin-2-yl)methyl)benzamide |

EXAMPLE 21

The compound prepared according to Example 20 is converted to flecainide by (1) reaction with ethylchloroformate to form the N-carboethoxypiperidinyl derivative, for example, by a procedure analogous to that described in U.S. Pat. No. 4,282,233, followed by (2) decarbalkoxylation by known methods, for example, by a procedure analogous to that described in U.S. Pat. No. 4,659,716.

EXAMPLES 22 AND 23

0.322 g (0.016 mole) of sodium metal is placed in a 250 ml three necked round bottom flask fitted with a condenser and a dropping funnel. 50 ml of dry ethanol are added with cooling. After the addition is complete, the mixture is warmed to complete the formation of sodium ethoxide. The sodium ethoxide solution is added to 1.32 grams (0.015 mole) of dry ethyl acetate in Example 22 (or 1.6.2 g (0.015 mole) of benzyl alcohol in Example 23) and brought to room temperature. The mixture is then heated to 50-55° C. for about one hour. The mixture is then cooled in an ice bath, and 0.016 mole of the α,α-dibromo-α-chloro acetophenone compound dissolved in toluene is added slowly. After the addition is complete, the mixture is brought to room temperature and stirred for 2 hours. The solvent is evaporated under vacuum and the residue dissolved in water, acidified and extracted with methylene chloride. The combined methylene chloride fractions are washed with saturated brine and dried over sodium sulfate. Finally, the solvent is removed to yield the product.

| # | acetophenone | nucleophile | product |
|---|---|---|---|
| 22 | Example 6 | ethylacetate | (structure: 2,5-dimethoxyphenyl β-ketoester ethyl ester) |
| 23 | Example 3 | benzyl alcohol | (structure: 2,5-bis(2,2,2-trifluoroethoxy)benzoic acid benzyl ester) |

We claim:

1. A process for the preparation of 2,5-bis(2,2,2-trifluoroethoxy)-N-(2-piperidylmethyl)-benzamide or a salt thereof, which comprises:

(a) reacting 2,5-bis(2,2,2-trifluoroethoxy)-α,α-dibromo-α-chloro acetophenone with 2-(aminomethyl)pyridine to form 2,5-bis(2,2,2-trifluoroethoxy)-N-(2-pyridylmethyl)-benzamide, and (b) reducing the 2,5-bis(2,2,2-trifluoroethoxy)-N-(2-pyridylmethyl)-benzamide.

2. A process of claim 1 wherein step (b) is carried out by exposing the 2,5-bis(2,2,2-trifluoroethoxy)-N-(2-pyridylmethyl)-benzamide to hydrogen in the presence of a hydrogenation catalyst.

3. A process of claim 2 wherein the catalyst is platinum-carbon.

4. A process of claim 1 wherein the 2,5-bis(2,2,2-trifluoroethoxy)-N-(2-piperidylmethyl)-benzamide is isolated as its acetate salt.

5. 2,5-bis(2,2,2-trifluoroethoxy)-α,α-dibromo-α-chloro-acetophenone.

6. A process for the preparation of 2,5-bis(2,2,2-trifluoroethoxy)-α,α-dibromo-α-chloro acetophenone which comprises reacting 2,5-bis(2,2,2-trifluoroethoxy)-α-chloro acetophenone with bromine.

7. A process of claim 6 wherein the 2,5-bis(2,2,2-trifluoroethoxy)-α-chloro acetophenone is prepared by reacting 1,4-di(2,2,2-trifluoroethoxy)benzene with 2-chioroacetyichioride in the presence of a Friedel Crafts catalyst.

8. A process of claim 7 wherein the Friedel Crafts catalyst is aluminum chloride.

9. A process for the preparation of 2,5-bis(2,2,2-trifluoroethoxy)-N-(2-pyridylmethyl)-benzamide which comprises reacting 2,5-bis(2,2,2-trifluoroethoxy)-α,α-dibromo-α-chloro acetophenone with 2-(aminomethyl)pyridine.

10. A compound of the formula

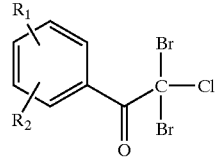

(II)

wherein $R_1$ and $R_2$ are independently hydrogen, $C_1$–$C_6$-alkyl, $C_3$–$C_7$-cycloalkyl, $C_1$–$C_6$-alkoxy, —N($C_1$–$C_6$-alkyl)$_2$, —S—$C_1$–$C_6$-alkyl, or phenyl, wherein the alkyl groups are unsubstituted or substituted by one or more halogen, hydroxy, —S—alkyl, —O—alkyl, carboxy, amido, or ester groups and when the $R_1$ or $R_2$ substituent is phenyl it is unsubstituted or substituted in the phenyl ring by halogen, $C_1$–$C_6$-alkyl, $C_3$–$C_7$-cycloalkyl, $C_1$–$C_6$-alkoxy, —N($C_1$–$C_6$-alkyl)$_2$, —S—$C_1$–$C_6$-alkyl, the alkyl groups of which are unsubstituted or substituted by one or more halogen, hydroxy, —S—alkyl, —O—alkyl, carboxy, amido, or ester groups; or $R_1$ and $R_2$ together with the phenyl ring carbons to which they are attached form a 5–7 member aliphatic, aromatic, heterocyclic, or heteroaromatic ring.

11. A compound of claim 10 wherein $R_1$ and $R_2$ are independently hydrogen, $C_1$–$C_4$-alkyl, $C_3$–$C_7$-cycloalkyl, $C_1$–$C_4$-alkoxy, —N($C_1$–$C_4$-alkyl)$_2$, or —S—$C_1$–$C_4$-alkyl; wherein the alkyl groups are unsubstituted or substituted by one or more halogen, hydroxy, —S—alkyl, —O—alkyl, carboxy, amido, or ester groups.

12. A compound of claim 10 wherein $R_1$ and $R_2$ are independently hydrogen, $C_1$–$C_4$-alkyl, $C_3$–$C_7$-cycloalkyl, or $C_1$–$C_4$-alkoxy wherein the alkyl groups are unsubstituted or substituted by one or more halogen, hydroxy, or —O—alkyl substituents.

13. A compound of claim 11 wherein at least one of $R_1$ and $R_2$ is substituted or unsubstituted $C_1$–$C_4$-alkyl; substituted or unsubstituted $C_3$–$C_7$-cycloalkyl; substituted or unsubstituted $C_1$–$C_4$-alkoxy; or substituted or unsubstituted —S—$C_1$–$C_4$-alkyl.

14. A compound of claim 11 wherein at least one of $R_1$ and $R_2$ is substituted or unsubstituted $C_1$–$C_4$-alkoxy.

15. A compound of claim 11 wherein $R_1$ is in the 4-position when $R_2$ is hydrogen, or $R_1$ is in the 2-position and $R_2$ is in the 5-position when $R_2$ is other than hydrogen.

* * * * *

UNITED STATES PATENT AND TRADEMARK OFFICE
CERTIFICATE OF CORRECTION

PATENT NO.   : 6,586,598 B2
DATED        : July 1, 2003
INVENTOR(S)  : Ray et al.

It is certified that error appears in the above-identified patent and that said Letters Patent is hereby corrected as shown below:

Column 11,
Line 58, should read -- 2-chloroacetylchloride in the presence of a Friedel Crafts --.

Signed and Sealed this

Twenty-first Day of October, 2003

JAMES E. ROGAN
*Director of the United States Patent and Trademark Office*